United States Patent [19]

Miura et al.

[11] Patent Number: 4,910,138

[45] Date of Patent: Mar. 20, 1990

[54] **USE OF AN ORGAN CULTURE OF *CATHARANTHUS ROSEUS* TO PRODUCE VINCRISTINE AND VINBLASTINE**

[75] Inventors: Yoshiharu Miura, Hyogo; Kazumasa Hirata, Osaka, both of Japan

[73] Assignee: Yoshiharu Miura, Hyogo, Japan

[21] Appl. No.: 858,122

[22] Filed: May 1, 1986

[30] Foreign Application Priority Data

May 2, 1985 [JP] Japan .................................. 60-95756

[51] Int. Cl.⁴ .......................... C12P 17/18; C12N 5/00
[52] U.S. Cl. ............................... 435/119; 435/240.45; 47/DIG. 3
[58] Field of Search ........................... 435/119, 240.45; 47/DIG. 3

[56] References Cited

U.S. PATENT DOCUMENTS

| | | | |
|---|---|---|---|
| 3,097,137 | 7/1963 | Beer et al. | 514/183 |
| 3,225,030 | 12/1965 | Sroboda | 540/478 |
| 4,569,914 | 2/1986 | Molnár et al. | 435/240.45 |

OTHER PUBLICATIONS

Kutney et al., *Heterocycles* 14(6): 765–768 (1980).
Stapfer et al., *HortScience* 20(1): 141–142 (Feb. 1985).
Krueger et al., *Planta Medica* 45:56–57 (1982).

*Primary Examiner*—Elizabeth C. Weimar
*Attorney, Agent, or Firm*—Birch, Stewart, Kolasch & Birch

[57] ABSTRACT

A method of preparing an organ culture from branched tissue of a *Catharanthus roseus* seedling is disclosed. The indole alkaloids vincristine and vinblastine can be recovered from the organ culture tissue via extraction.

1 Claim, No Drawings

USE OF AN ORGAN CULTURE OF *CATHARANTHUS ROSEUS* TO PRODUCE VINCRISTINE AND VINBLASTINE

The invention relates to the production of indole alkaloids by cultivating organ culture of *Catharanthus roseus* (periwinkle).

*C. roseus* has been previously known to produce as secondary metabolic products various indole alkaloids useful as an antitumor, hypotensive or antiarrhythmic agent, and many attempts to produce and recover said alkaloids from the tissue culture of the plant have long been made. The applicant of the present application succeeded in preparing a callus from the plant and recovering the alkaloids from the callus (See Japanese Patent Application Ser. Nos. 85228/1982 and 197412/1982). However, such callus is not satisfactory as a stable supply source of the alkaloids because the alkaloid productivity of the callus is liable to gradually decrease due to the following reasons:

(1) Secondary metabolic products in most plants are associated with organogenesis and are generally produced only in particular organ(s). In other words, such metabolic products are produced by plant cells which have acquired, and are retaining, secondary metabolic activity as a result of "physiological differentiation". Since callus cultures are those which have been compulsorily dedifferentiated by a phytohormone, they often lack such secondary metabolic activity resulted from the physiological differentiation.

(2) Secondary metabolic products are not necessary for cell growth. Accordingly, in callus culture, the cells having no or inferior secondary metabolic activity become predominant during repeated subcultures.

Contrary to the callus cultures mentioned above, an organ culture, which starts from a particular organ of a plant, is generally recognized to retain secondary metabolic activity possessed by the parent plant. The organ culture is a culture system uniquely differentiated from a dedifferentiated or pre-differentiated tissue so as to develop a particular organ such as a stem, leaf, root or the like. The culture system thus obtained can be subcultured or massively cultured to produce various useful materials. The organ cultures of *Papaver somniferum* (see T. Yoshikawa and T. Furuya, Planta Medica, 1985(2), 110-113) and Digitalis *purpurea* (see J. H. C. Lui and E. J. Staba, Phytochemistry 18, 1913-1916(1979); M. Hagimori, T. Matsumoto and Y. Mikami, Agric. Biol. Chem. 48, 965-970(1984)) are examples which succeeded in producing desired products in an increased amount. However, production of useful materials by means of an organ culture is usually associated with the following problems.

(i) An organ-differentiation ability varies from plant to plant and, therefore, an organ culture process is not necessarily applicable to all sorts of plants.

(ii) Where the secondary metabolic activity, i.e., a producing ability for a desired product is localized in a particular organ, it is necessary to selectively differentiate and grow said organ.

*C. roseus* is known to be a plant hard to be artificially differentiated and no stable organ culture has been established yet, although reproduction of the whole plant, induction of a shoot tissue and its cultivation in a liquid medium have been reported. The induction of the shoot tissue mentioned above was made using callus and is far from a practical use for producing indole alkaloids because an induction frequency is very low and the induction from the callus takes a lot of time.

It has now been found that an organ culture having high productivity of alkaloids is obtained by cultivating under light irradiation a seedling of *C. roseus* on a culture medium containing phytohormone, transferring branched tissue projected from a dicotyledonous portion of the seedling to the same culture medium, and cutivating said branched tissue. The alkaloids produced by the organ culture of the invention are composed of various indole alkaloids such as vinblastine, vincristine, vindoline, catharanthine, ajmalicine, and the like, which are all found in the parent plant.

Vinblastine and vincristine are well known to be useful as antitumor agents. Vindoline and catharanthine are major alkaloids of *C. roseus* and are intermediate compounds of vinblastine and vincristine. Ajmalicine is converted, by oxidation, to serpentine which has hypotensive activity. Vindoline, catharanthine and ajmalicine are also useful as a hypoglycemic, diuretic or hypotensive agent.

A mixture of these indole alkaloids will be referred to as "*C. roseus* indole alkaloids" hereinafter.

Accordingly, the present invention provides a method for producing *C. roseus* indole alkaloids which comprises cultivating under light irradation a seedling of *C. roseus* on a culture medium containg phytohormone, transferring branched tissue projected from dicotyledonous portion of the seedling to the same culture medium, cultivating said branched tissue, and recovering alkaloids from the resultant organ culture.

The invention also provides *C. roseus* indole alkaloids produced by the above process of the invention.

The invention further provides an organ culture induced from *C. roseus* by the above-mentioned method, said culture being capable of producing substantial amounts of *C. roseus* indole alkaloids.

The process for inducing an organ culture from *C. roseus* and the process for recovering the indole alkaloids produced by the organ culture will be detailed below.

According to the preferred embodiment of the present invention, Madagascar *C. roseus* is employed as a starting material. Seed of Madagascar *C. roseus* is sterilized on the surface, placed on sanitary cotton moistened with distilled water, or Murashige-Skoog medium, containing 0.55% by weight of agarose, and allowed to germinate under sterilized conditions. A whole seedling in dicotyledon-forming stage, 7 to 10 days after germination, was transferred to Murashige-Skoog medium containing 0.55% by weight of agarose and phytohormone, and the seedling is cultivated at 25° C. under irradiation of monolux light (about 1000 lux). After one or two weeks, projection of branched tissue is initiated at the dicotyledonous portion and a lot of shoots are developed. The developed shoots are cut off and subcultured on the same medium as above to obtain a stable organ culture. In order to induce an organ culture, phytohormone such as benzyladenine is added to the medium at the concentration of 0.1-10 mg/liter, preferably, 1.0 mg/liter. Alternatively, the induction of an organ culture can be achieved by direct cultivation of the seed in the medium supplemented by the phytohormone. As will be readily understood by those skilled in the art, subcultures can be carried out by either a surface or liquid culture.

Where the shoot organ is transferred to, and cultivated in, a liquid medium of the same compositions as above or, where the shoot organ is cultivated on an agarose surface medium supplemented with benzyladenine and 0.01-1.0 mg/liter of auxin, such as indoleacetic acid (IAA) or naphthaleneacetic acid (NAA), the growth of culture is accelerated 2 or 3 times as compared with the case where the surface medium supplemented with benzyladenine alone is employed. Such accelerated growth may be also attained by suitably adjusting medium compositions, cultivation temperature, intensity and duration of light irradiation.

The induction frequency of the organ culture of the invention is greater than 80% because the organ culture is directly induced from the seedling without passing a callus stage. In addition, the induction to a stable organ culture requires relatively short time, for instance, about 2 months from the germination. Although C. roseus alkaloids are found in every organ and tissue of the plant, the leaf has the highest contents of the alkaloids. Accordingly, the organ culture uniquely differentiated to a shoot organ may produce the alkaloids more efficiently than previously-known cell cultures. The shape and growth rate of the organ culture of the invention can be controlled by adjusting the amount of phytohormone to be added to the medium and/or culture conditions. According to the invention, a liquid culture is preferred because the growth rate of the liquid culture is several times greater than that of a surface culture and, therefore, the former is suitable for a mass production of the C. roseus alkaloids.

The total alkaloids content in the dried organ culture of the present invention amounts to about ⅓ of that of the leaf tissue of the parent plant by weight/weight basis. On the other hand, for instance, vinblastine content in the dried organ culture is about 1/5 to 1/20 of that found in the leaf. However, in the light of the increased growth rate of the organ culture of the invention, the production efficiency of the alkaloids possessed by the organ culture is extremely higher than that of the parent plant.

If desired, it is possible to induce and differentiate a root from the shoot organ culture so as to regenerate a whole plant. It is also possible to induce a photoautotrophic culture by removing carbon sources from the culture medium.

Recovery of the alkaloids from the shoot organ culture can be conducted in a conventional manner. For instance, the organ culture is lyophilized and extracted with methanol for 1 to 3 days. Evaporation to dryness of the resulting extract gives crude alkaloids as the residue. The residue containing the crude alkaloids is dissloved in a phosphate buffer (pH 7.4) and employed as a sample for a radioimmunoassay described hereinafter.

As previously mentioned, the alkaloids content of a callus culture is relatively low. For instance, the maximum of vinblastine content found in our experiments is 10 μg/g (dired callus weight). In addition, repeated subculture of the callus leads to a rapid decrease of the alkaloids content. Thus, no alkaloid is found in a callus which has been subcultured over several months. On the contrary, the organ culture of the invention has a high content of alkaloids as illustrated in the following Example, wherein vinblastine content of 90 μg/g (dried tissue weight) was obtained from the initial organ culture. The culture of the invention also retains its shape and alkaloids content during repeated subcultures. Accordingly, the organ culture of the invention provides a means affording various alkaloids useful as an antitumor, hypotensive, antiarrhythmic agent, or the like.

The following detailed example is presented by way of illustration of certain specific embodiments of the invention.

EXAMPLE 1

(1) Induction of shoot organ and its cultivation

A seed of Madagascar C. roseus was sterilized on the surface by the use of 1% NaOCl and allowed to germinate on sanitary cotton moistened with water to obtain the seedling. The seedling was transferred to Murashige-skoog medium containing 0.55% by weight of agarose and cultivated at 25° C. under irradiation of monolux light (about 1000 lux). The seedling did not grow normally and, a lot of branched tissues were developed and projected at the dicotyledonous portion of the seedling. The branched tissues were cut off and cultivated under the same conditions mentioned above. The branched tissues grew actively to give a stable shoot organ culture and gained 10 times weight of the initial weight in one month cutivation.

(2) Assay of indole alkaloids produced by organ culture (i) Assay of vinblastine Vinblastine content of the organ culture obtained above and the parent plant were determined by radioimmunoassay in a conventional manner. The result is shown in Table 1.

TABLE 1

| Material | Benzyladenine added (mg/l) | Vinblastine Content (μg/g dry weight) |
|---|---|---|
| Organ culture (No. 1) | 0.5 | 96.0 |
| Organ culture (No. 2) | 1.0 | 89.3 |
| Parent plant (No. 1) | — | 2100 |
| Parent plant (No. 2) | — | 1320 |

The above test revealed that the vinblastine content of the organ culture ranges from 1/10 to 1/20 of that in the parent plant.

(ii) Assay of other indole alkaloids

Other indole alkaloids than vinblastine contained in the organ culture, i.e., vindoline, catharanthine and ajmalicine were assayed in the following manner.

In accordance with the method described by J.- P. Renandin, J. Chromato., 291 165, 1984, the indole alkaloids were extracted from the organ culture and subjected to a high performance liquid chromatography (HPLC) to determine their contents.

Identification and separation of a particular alkaloid in the crude alkaloids extract were also performed by thin layer chromatograghy (TLC) using Kieselgel 60 $F_{254}$ (Merk) as a carrier and a mixture of ethyl acetate : ethanol (1:1) as a developing solvent. Detection of alkaloids on TLC was carried out by U.V. light irradiation, or by spraying ceric ammonium sulfate solution, and particular alkaloid was identified on the basis of Rf value comparing with that of an authentic sample.

The HPLC and TLC analysis revealed that vindoline, catharanthine and ajmalicine contents in the organ culture of the invention are respectively about 12 mg, 3 mg and 0.3 mg/g dry weight of the organ. The vindoline content was found to be substantially the same as that of the parent plant, while catharanthine content was about 10 times higher than that of the plant, and ajmalcine content was about 1/10 to 1/50 of the plant.

(iii) Assay of total alkaloids

The total alkaloids produced by the organ culture of the invetion were assayed by "methyl orange" method (see A. O. Gettler and I. Sunshine, Anal. Chem., 23, 779-781 (1951)). The total alkaloids content was 0.2 % on the basis of dry weight of the the organ culture which corresponds to ⅓ of that of the parent plant. The total alkaloids are supposed to include vincristine together with aforementioned alkaloids.

What is claimed is:

1. A process for the preparation of vinblastine and vincristine which comprises cultivating a seedling of *Catharanthus roseus* on a culture medium containing a phytohormone, transferring branched tissue projected from a dicotyledonous portion of said seedling to said culture medium, cultivating said branched tissue, and recovering said vinblastine and vincristine from the resultant culture by extraction.

* * * * *